US008540168B2

(12) United States Patent
Bennett et al.

(10) Patent No.: US 8,540,168 B2
(45) Date of Patent: Sep. 24, 2013

(54) WICK FRAGRANCE DIFFUSER

(76) Inventors: Gregory Bennett, Chiang Rai Province (TH); Aksornsil Kaewbudda, Chiang Rai Province (TH)

( * ) Notice: Subject to any disclaimer, the term of this patent is extended or adjusted under 35 U.S.C. 154(b) by 450 days.

(21) Appl. No.: 12/639,281

(22) Filed: Dec. 16, 2009

(65) Prior Publication Data

US 2010/0147969 A1    Jun. 17, 2010

Related U.S. Application Data

(60) Provisional application No. 61/138,394, filed on Dec. 17, 2008.

(51) Int. Cl.
*A24F 25/00* (2006.01)
*A61L 9/04* (2006.01)

(52) U.S. Cl.
USPC .................. 239/43; 239/50; 239/53; 239/145

(58) Field of Classification Search
USPC ................. 239/34, 43, 44, 45, 49–50, 53–56, 239/145–326
See application file for complete search history.

(56) References Cited

U.S. PATENT DOCUMENTS

| 4,958,768 A * | 9/1990 | Ishihara ........................... 239/34 |
| 6,565,012 B1 * | 5/2003 | Zaragoza et al. ................ 239/44 |
| 7,488,703 B2 * | 2/2009 | Rubin ............................ 504/359 |
| D596,732 S * | 7/2009 | Butler et al. .................. D23/366 |
| 2001/0030243 A1 * | 10/2001 | Hurry et al. ..................... 239/60 |
| 2010/0301128 A1 * | 12/2010 | Pisklak .............................. 239/6 |

* cited by examiner

*Primary Examiner* — Len Tran
*Assistant Examiner* — Justin Jonaitis
(74) *Attorney, Agent, or Firm* — Howard B. Rockman

(57) ABSTRACT

A fragrance diffuser and method of adjusting the evaporation rate of fragrance from a diffuser includes a container having an opening communicating with the interior of the container. A quantity of granular solids material such as silica sand, calcium carbonate sand, salt or starch is located in the container, and a fragrance material is mixed with the solids material to form a solids material-fragrance material mixture that is free of solvents, or includes a minor amount of a low volatility solvent. Wicking material is inserted through the opening of the container, and a portion of the wicking material is immersed into and supported by the solids material-fragrance material mixture. The fragrance material migrates along or through the wicking material and evaporates into the surrounding environment. The evaporation rate of fragrance from the diffuser can be adjusted by varying the length of the wicking material immersed into the granular solids material-fragrance mixture.

19 Claims, 1 Drawing Sheet

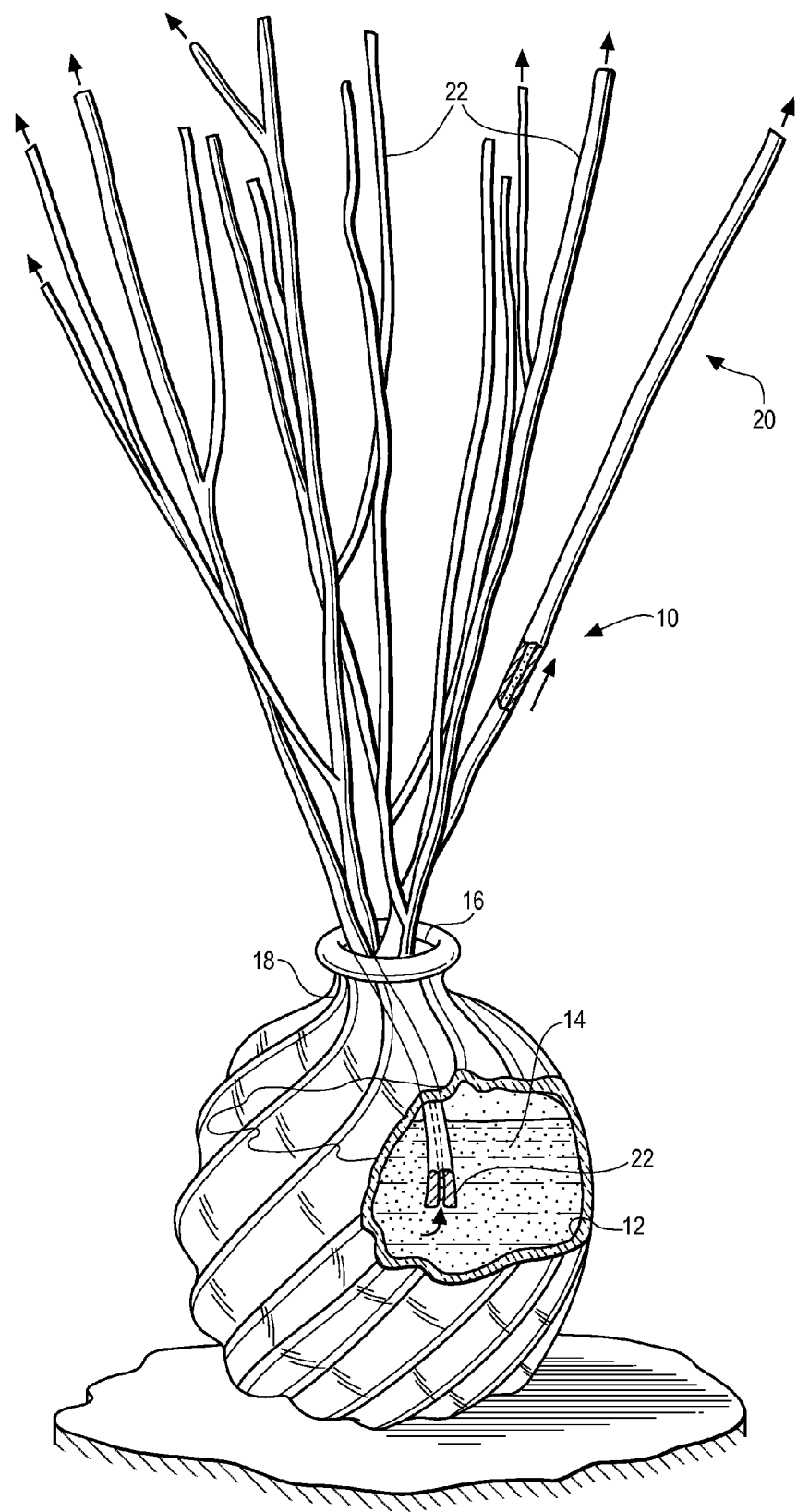

WICK FRAGRANCE DIFFUSER

This application claims priority to and is a continuation-in-part of provisional patent application Ser. No. 61/138,394 filed Dec. 17, 2008 to the extent allowed by law.

The present invention is an improved wick diffuser that odorizes an environment without the use of solvents, or using a minor amount of low volatility solvent. More particularly, the present invention comprises a combination of a fragrance and in certain embodiments, a pre-treated granular amorphous or crystalline solids material mixture into which a wicking material has been partially immersed, such that the fragrance material evaporates into the atmosphere surrounding the wicking material and odorizes the atmosphere. The solids mixture forming part of the present invention comprises silica sand, calcium carbonate sand, salt or starch, among others.

BACKGROUND OF THE INVENTION

Numerous wick-type diffusers are presently available. These diffusers typically comprise a one to sixteen ounce container, such as a glass vase, bottle, or other suitable container filled or partially filled with a fragrance material combined with solvents. A typical diffuser uses a 6-7 ounce container. A wick, such as a natural reed, branch or cotton wick, natural sponge or synthetic polymer foam, protrudes out of the container to allow the fragrance to evaporate into the surrounding air. Solvents used in presently available diffusers typically include, among others, alcohol, or heavy solvents such as petroleum distillates, glycol ethers, phthalate and adipate solvents, ISOPAR hydrocarbon solvents, carbitols, cellosolves, downanols and dipropylene glycol methyl ether.

Currently marketed fragrance diffusers utilize solvents for several reasons. To make the final product appear larger and fuller, these solvent-based diffusers typically include 10%-50% fragrance in containers that may hold 6.5 ounces of liquid. Producers use solvents to fill the remainder of the container with a liquid material that is less costly than pure fragrance materials. These prior diffusers also are made with heavy solvents having evaporation rates less than 0.1 mm Hg to comply with current anti-smog volatile organic chemical (VOC) limitations imposed by law. The manufacturers of these presently available diffusers also claim that solvents are used to control the rate of evaporation of the product. However, presently available diffusers do not evaporate well. They evaporate poorly through the wicking material as the wick becomes saturated with non-evaporative solvents.

The aforementioned, and other, solvents can be dangerous to human health and, since they do not evaporate, hazardous to the environment when emptied into sewage drains and the like. This is particularly significant because millions of pounds of these solvents are disposed of annually. Once the fragrance in these diffusers has evaporated, the hazardous solvents are left behind and normally would have to be disposed of properly and not in a landfill or drain. Hazardous conditions can also result if the container of solvent-fragrance liquid is tipped over and a spill results.

Additionally, existing fragrance diffusers use fragrance mixtures that do not evaporate well through the wicking material. Frequently, to make current products last longer, the users of such diffusers are instructed to flip the reeds by placing the portion of the wicking material that was previously exposed to the atmosphere into the solvent-fragrance mixture, whereby the previously submerged portion of the wick is now exposed to the atmosphere. This procedure is highly detrimental to the performance of the diffuser, and produces a myriad of undesirable results for the user. Flipping the wick material typically results in splashing the fragrance and solvent mixture outside of the container and onto the table or other surface supporting the diffuser.

Also, flipping the wick material typically only continues the odor production of the product for one to seven days, and then the odor level dies down again. This occurs because as the fragrance and solvent system is advancing up the wicking material, and the fragrance is evaporating, the non-volatile solvent becomes concentrated in the exposed portion of the wick. Eventually excessive amounts of heavy solvents remain, with very little fragrance in the wick. After the wick is flipped, the previously submerged portion of the wick is now exposed, but fragrance evaporation continues for only a short period of time.

Further, in present wick-type diffusers, the wick can be easily knocked out of place and damage furniture, carpets, or other surfaces upon contact with the solvent-fragrance mixture. The spilt mixture could also present a human health hazard, as mentioned above.

Due to the flammable and/or combustible nature of most solvent-fragrance mixtures used in present diffusers, with flash points below 155 degrees Fahrenheit, manufacturers must provide a warning label on these products so the user does not place the diffuser near a flame or in a high heat location. Some manufacturers of current diffusers attempt to raise the flash point of their solvent-fragrance mixture by diluting the product with heavy, non-evaporative solvents. This procedure results in a trade off that either potentially damages the environment, or causes the performance of the diffuser to be radically diminished. When the consumer decides that such products have outlived their useful life, there is a tendency to pour the remaining solvent into the drain, causing potential harm to the environment.

An object of the present invention is to overcome all of the above described problems of other diffusers by providing a solvent-free diffuser, or a diffuser comprising only a minor amount of a low volatility solvent, that does not provide potential human health problems or environmental hazards, and yet is attractive, stable and long lasting.

A further object of the present invention is to provide a fragrance diffuser that firmly supports a reed wick, and wherein the fragrance material is specifically formulated to provide optimum fragrance release with the specific reed wick material used in the diffuser.

Another object of the present invention is to allow the fragrance evaporation rate into the adjacent environment to be adjusted by the user without flipping the reed wick. Additionally, the presently disclosed diffuser can be reused, refilled and will continue to function as new.

SUMMARY OF THE INVENTION

These and other objects are provided in a diffuser that includes a container typically made of a decorative glass, ceramic or other material. The container is filled or partially filled with a pre-treated granular amorphous or crystalline solids material and fragrance mixture that is solvent free, or comprises only a minor amount of a low volatility solvent. A wick, such as a natural reed, branch or cotton wick, polymer foam, a synthetic reed, or natural sponge, is inserted into the solids material and fragrance mixture. The active fragrance advances up the wick and evaporates into the atmosphere as is known in the diffuser art. The present invention utilizes only fragrance materials that can be evaporated by the wick material. The pre-treated solids material enables the fragrance to have increased longevity and a reduced evaporation rate. The weight of the solids material in the container also stabilizes the container and prevents the diffuser from being easily dislodged or tipped over. The wicks used in the present invention are biodegradable and are also specially treated with fragrance, allowing the fragrance to migrate through the wick and evaporate at a uniform rate.

BRIEF DESCRIPTION OF THE DRAWING

FIG. 1 is a front elevation view of the diffuser of the present invention illustrating a glass container filled or partially filled with a pre-treated granular solids material and fragrance mixture, and a wick material extending into the solids material and fragrance mixture and partially extending outward from the container into the surrounding atmosphere.

DESCRIPTION OF THE ILLUSTRATED EMBODIMENT

Referring to FIG. 1, the present invention is a wick diffuser generally designated by the numeral 10. In the illustrated embodiment, a decorative bottle 12, transparent or opaque, is filled, or partially filled, with an amorphous or crystalline solids material and fragrance mixture 14, where the solids material in an embodiment has been pre-treated with a fragrance formulation, as will be explained. Amorphous solids material may include silica sand, calcium carbonate sand, and starch. Crystalline solids material may include salt (sodium chloride). Other solid materials may be used in the present invention. In an embodiment, the solids material also includes gypsum in the amount of less than one percent by weight. Any other fluid holding container, such as a tin can, clay or ceramic pot, or the like may also be used in place of bottle 12.

The bottle 12 has an opening 16 formed atop a neck 18, such that opening 16 communicates with the interior of bottle 12. A wicking material 20, shown comprising one or more natural reeds or branches 22 in the illustrated embodiment, extends through opening 16 of bottle 12, and the wicking material has a lower portion immersed in the solids material and fragrance mixture 14. A cotton wick could also be substituted for the wicking material 20 of FIG. 1, and possibly a synthetic polymer or foam, or natural sponge material could be used as a wicking material. The evaporation rate of fragrance from the diffuser into the atmosphere can be adjusted by partially inserting the wicking material 20 into or out of the solids material and fragrance mixture 14 to achieve the desired evaporation rate and degree of scent in the surrounding environment. Since the mixture 14 supports the wick material 20 in any variable position, the present invention provides a decided advantage not found in liquid filled diffusers. As will be discussed in further detail, the fragrance in the solids material and fragrance mixture 14 migrates up the wicking material 20, and the fragrance then evaporates and odorizes the surrounding environment.

In the present invention, liquid or combined liquid-solid fragrances may be utilized in the illustrated embodiment that are compounded from two or more synthetic and/or natural chemicals and/or essential oils for the purpose of producing an aroma. These fragrances fall into categories such as fruity, floral, aldehydic, woody, musky, spicy, fern, sweet and others. By way of example, a woody-floral fragrance used in the present invention would be:

| Lavender Essential Oil | 15% |
|---|---|
| Linalool | 25% |
| Linalyl Acetate | 5% |

-continued

| Phenyl Ethyl Alcohol | 25% |
|---|---|
| Geraniol | 10% |
| Citronellol | 5% |
| Cedarwood Essential Oil | 5% |
| Lemon Oil | 10% |

This fragrance could expect to emit a lavender-rose aroma with woody notes. Initially, the aroma would be more lavender, and at the end of its life, the fragrance would become more woody and camphoric.

A further example of a fragrance that can be used with the present invention is:

| Cinnamic Aldehyde | 22% |
|---|---|
| Orange Peel Oil | 10% |
| Clove Leaf Essential Oil | 20% |
| Eugenol | 5% |
| Nutmeg Essential Oil | 3% |
| Ginger Essential Oil | 5% |
| Amyl Cinnamic Aldehyde | 20% |
| Vanillin | 5% |
| Ethyl Vanillin | 5% |
| Coumarin | 5% |

This fragrance compound produces an expected aroma mixture of cinnamon and spices reminiscent of holiday foods such as pumpkin pie.

The fragrances used in the present invention are designed to fully evaporate through the wicking material 20 and be released into the atmosphere. The selected fragrance compounds avoid using low vapor pressure solvents, solvents that are hydrophilic, or fragrance raw materials that have a low vapor pressure and may not evaporate over a span of a year. The present invention is generally formulated to be solvent free, however, a minor amount of low volatility solvent may be included in the fragrance.

In the present invention, the granular amorphic or crystalline solids material is pre-treated before use with the selected fragrance only. There are no, or only a minor amount of low volatility solvent in the solids material-fragrance mixture. In the production process of certain embodiments of the invention, the solids material is washed with soap and water to produce a dry, clean mass. The granules of solids material used in the present invention are a minimum size so that the reeds or wicks 20 can be inserted into, and are supported by, the solids material and fragrance mixture 14. For example, solids materials such as ISO 14688 grade sand as fine (0.063 to 0.2 mm), medium (0.2 to 0.63 mm) and coarse (0.63 to 2.0 mm) can be used. The present invention uses solid materials in the range of 0.2 mm to 1.0 mm in diameter. The solids material may or may not contain gypsum or other minerals. It has been determined that a small percentage of gypsum, in the range of less than 1%, could be useful in controlling the fragrance diffusion rate.

If desired, dyes can be added to the solids material-fragrance combination 14 in the bottle 12 to alter the appearance of the product in a translucent bottle. The dyes can be natural vegetable dyes or synthetic dyes. The reeds or wicks 20 may also be dyed to alter their appearance.

In the illustrated embodiment, assuming a bottle 12 having a capacity of 250 ml, 50 to 100 grams of fragrance and from 100 to 500 grams of solids material would be inserted into the bottle. If the granular solids material is very coarse, smaller amounts of solids material and more fragrance form the solids material-fragrance mixture 14. For example, in an embodiment, 100 grams of fragrance would be mixed with 200 grams of coarse solids material. If the solids material is very fine, less fragrance and more solids material is used. For example, 85 grams of fragrance and 360 grams of fine granular solids material. If desired, small rocks or pebbles, sea glass, or other decorative elements could be blended into the solids material-fragrance mixture 14 for decorative purposes. The maximum ratio of solids material to fragrance used to form solids material-fragrance mixture 14 of the present invention is 10:1, and the minimum ratio is 1:1. An optimum ratio is approximately 4:1.

The present invention in an embodiment also maintains the solids material and fragrance ratio such that the upper level of fragrance is below the upper level of the solids material in the container, and the fragrance is blended with and contained in the solids material. This is different from previous liquid filled reed diffusers comprising approximately eight ounces of fragrance fluid that can be hazardous if the diffuser container is tilted, knocked over, or broken. In the present invention, the weight of the solids material prevents the bottle 12 from tilting or spilling easily.

Additionally, if a spill does occur, it will take some time for the liquid fragrance to migrate out of the solids material, providing time to clean up any spilled liquid that may have worked its way out of the solids material. If the bottle 12 of the present invention is momentarily turned on its side, only a small amount of liquid, or no liquid, will emerge from the bottle, and additional liquid will take some time to leave the solids material. Alternately, the level of the fragrance may be above the level of the solids material initially, but after the reeds are inserted into the solids material and fragrance mixture and the reeds begin to absorb fragrance, the level would rapidly drop below the level of the solids material, expectedly within a few hours.

In the present invention, the fragrances used are created to evaporate fully over the intended life of the product. The fragrances are created by combining synthetic and natural chemicals, oils, and resins from plants. For example, a musk compound with a low volatility would need to be used sparingly and in conjunction with higher volatile citrus oils to ensure all evaporate in the time allotted and that the fragrance is balanced for odor and evaporation rate. Some fragrance chemicals with minor or low volatility may be used since they are carried off into the environment as the lighter, more volatile chemicals evaporate. Some light fragrance components can be used as they become depressed by the heavier elements in the mixture.

The balance is important, as well as the residuals. If the fragrance in mixture 14 comprises excessive amounts of low volatility components, the solids material may retain these components after the intended life of the product. The fragrance preferably is balanced so that these residuals do not exist or are minimized. For the larger components, chemicals or fragrance mixtures having a vapor pressure of about 0.2 mm Hg should be selected, such as lavender essential oil, for example. If linalool, which has a low vapor pressure of 0.1 mm Hg were selected, a balance could be achieved by incorporating a chemical having a much higher vapor pressure, such as orange oil at 2.00 Hg by way of example. Other light essential oils, or citrus oils, or both, can also be used with linalool.

In designing a fragrance mixture to work with the diffuser 10, mismatches will result in substituting replacement chemicals. For example, if a chemical having an undesirably high vapor pressure is chosen, it will be prudent to use only a small amount to achieve the target aroma. Or, a large amount of chemical having a very low vapor pressure may be selected in place of a chemical with a higher vapor pressure, if the remaining chemicals have a high average vapor pressure.

Vapor pressure, weight of the fragrance molecules and polarity are all factors related to the evaporation rate, as is known to those of ordinary skill in the art. Also, combinations of different chemicals can also have an effect upon the evaporation rate of the fragrance chemical mixture. The diffuser of the present invention uses only fragrance materials that can be evaporated by the reeds, along with the solids material, colorants, and a trace of stabilizers such as UV inhibitor, BHT, and citric acid, for example.

In creating the proper fragrance to be utilized with diffuser 10, attention must be paid to the evaporation rate and vapor pressure of the fragrance mixture, and the proper balance between all factors must be maintained to achieve the desired aroma and fragrance life.

The reeds or wicking material 20 used in the diffuser 10 of the present invention are made of several select materials. One such material is a core of rattan with the outer cover, or bark, removed. In the illustrated embodiment, the rattan reeds are dried and are also bleached. It has been discovered that bleaching improves the ability of the reed to evaporate high amounts of fragrance compared to unbleached reeds. It has also been discovered that larger fragrance chemicals, such as musk, for example, provide better results in bleached reeds.

The present invention, in certain embodiments, includes pre-treating the reeds upon use with a fragrance that contains natural essential oils, such as orange, lime, grapefruit, lemon, clove, lavender, and pine by way of example. The pre-treatment has been seen to prohibit the growth of mold on the reeds, and to allow the reeds to immediately begin working when the reeds 20 are inserted into the solids material and fragrance mixture 14. Normally, untreated reeds take twenty four hours or more to become saturated and start the diffuser 10 working. Since the reeds 20 of this embodiment of the present invention are pre-infused with fragrance oils and essential oils, the reeds begin to generate an aroma as soon as they are unwrapped. The pretreatment of the reeds 20 can be with the same fragrance combined with the solids material, a mixture of essential oils, a combination of the same fragrance and the mixture of essential oils, or a similar fragrance that would provide the consumer with a near sampling of the fragrance to be combined with the solids material after purchase, but which similar fragrance does not fully evaporate during the shelf life of the diffuser 10.

As the fragrance and essential oils evaporate from the reeds, the reeds begin to draw up and replace fragrance from the solids material-fragrance mixture 14 in container 12. Rattan reeds 20 have a cellular structure, and if the cells are not pre-treated with fragrance chemicals, the capillary action to draw the fragrance into the reeds does not start immediately upon immersion of the reeds into the solids material-fragrance mixture 14. In liquid-based reed diffusers without pre-treated reeds, the reeds are required to sit in the liquid for a considerable time before the fragrance chemicals migrate into the reed and eventually evaporate into the environment.

The pretreatment of the reeds 20 of the present invention allows the diffuser 10 and reeds 20 to be packaged so the consumer can experience the diffuser fragrance at the point of purchase. The packaging for the diffuser 20 of the illustrated embodiment includes a scent port in the packaging adjacent a portion of the reeds in the package. The consumer can smell the aroma of the pre-treated reeds through the scent port prior to selecting the product.

Once the fragrance has fully evaporated, the sand or other solids material can be reused by adding additional fragrance chemicals or essential oils to the solids material in the diffuser container. Even if the sand is discarded after full evaporation, the absence of solvents in the diffuser frees the solids material of any hazardous chemicals. If the diffuser 10 is tipped over before full evaporation, the solids material slows the movement of the fragrance, and only a minimal amount of liquid, or no liquid, will spill from container 12.

The solids material allows the fragrance level in an environment to be adjusted by the user, as mentioned previously. If a light fragrance aroma is desired, the wicking material or reed 20 is inserted only a short distance into the solids material-fragrance mixture 14. To achieve the full effect of fragrance evaporation from the wick or reed 20, the wick or reed is immersed further into the sand-fragrance mixture. Additionally, the wicks or reeds 20 are securely held in place by the sand and resist becoming dislodged when container 12 undergoes an accidental impact. Additionally, the granular solids material allows the user to adjust the height of the reeds to vary the overall appearance of the diffuser.

In a further embodiment of the present invention, the solids material is coated before use in the diffuser with resin, lacquer, enamel, latex or polymers. Typically these coatings impart color to the solids material, providing various decorative effects. If desired, the solids materials can remain pure and uncoated, as described above.

In the embodiment of the present invention where the solids material is salt, the diffuser 10 has the added advantage of the salt being able to be washed down the drain without harming the environment. Also, due to the crystalline structure of the salt, it provides a reduced evaporation rate compared to the other solids materials that can be used with the present invention.

The foregoing description of an illustrated embodiment of the invention has been presented for purposes of illustration and description, and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated. It is intended that the scope of the invention not be limited by the specification, but be defined by the claims set forth below.

We claim:

1. A fragrance diffuser comprising:
   a) a container having an opening communicating with an interior of the container, a quantity of solids material disposed in the interior of the container, said solids material comprising granules of a substantial minimum size;
   b) a fragrance material mixed with the solids material to form a solids-fragrance material mixture;
   c) at least one element of wicking material inserted into the container through the opening in the container, the at least one element of wicking material having a portion immersed into the combination of the fragrance material and the solids material;
   d) the solids-fragrance material mixture in the container contacting the wicking material, the wicking material portion that is immersed into the solids-fragrance material mixture being held in place, in any variable position of the wicking material, through the interaction between the wicking material and the granules of the solids material;
   e) the fragrance material migrating along said at least one element of wicking material, said fragrance material evaporating into the environment surrounding the container and creating an aroma in the environment surrounding the container.

2. The fragrance diffuser of claim 1, wherein:
said liquid fragrance material is free of solvents.

3. The fragrance diffuser of claim 1, wherein:
said liquid fragrance material includes a minor amount of a low volatility solvent.

4. The fragrance diffuser of claim 1, wherein said fragrance material is a liquid.

5. The fragrance diffuser of claim 1, wherein:
said fragrance material is a combination of liquid-solid fragrance materials.

6. The fragrance diffuser of claim 1, wherein:
said solids material is a granular solids material.

7. The fragrance diffuser of claim 1, wherein:
said solids material is selected from the group consisting of amorphous solids material and crystalline solids material.

8. The fragrance diffuser of claim 7, wherein:
said solids material is selected from the group consisting of silica sand, calcium carbonate sand, and starch.

9. The fragrance diffuser of claim 7, wherein:
said solids material is salt.

10. The fragrance diffuser of claim 1, wherein:
said solids material is pretreated with a fragrance material prior to use.

11. The fragrance diffuser of claim 1, wherein:
the at least one element of wicking material is pretreated with a fragrance material prior to use.

12. The fragrance diffuser of claim 1, wherein:
the amount of fragrance emitted by the diffuser is adjusted by modifying the position of the portion of the wicking material immersed into the solids fragrance material mixture.

13. The fragrance diffuser of claim 1, wherein:
said wicking material is selected from the group consisting of natural reed, natural branch, cotton, synthetic polymer, and natural sponge.

14. The fragrance diffuser of claim 1, wherein:
said fragrance material comprises fragrance elements selected from the group consisting of synthetic fragrance chemicals, natural chemical elements, plant resins, and essential oils.

15. The fragrance diffuser of claim 1, wherein:
said wicking material is bleached.

16. The fragrance diffuser of claim 1, wherein:
the solids material includes gypsum in the amount of less than 1 percent by weight.

17. The fragrance diffuser of claim 1, wherein:
the ratio of solids material to fragrance material in said solids fragrance material mixture is in the range of 1:1 to 10:1.

18. The fragrance diffuser of claim 1, wherein:
the ratio of solids material to fragrance material in said solids fragrance material mixture is approximately 4:1.

19. The fragrance diffuser of claim 1, wherein: the granules comprising the solids material are in the size range of 0.2 mm to 1.0 mm in diameter.

* * * * *